(12) United States Patent
Delevati et al.

(10) Patent No.: US 12,077,659 B2
(45) Date of Patent: Sep. 3, 2024

(54) BIO-BASED ELASTOMERIC EVA COMPOSITIONS AND ARTICLES AND METHODS THEREOF

(71) Applicant: Braskem S.A., Camaçari (BR)

(72) Inventors: Giancarlos Delevati, São Paulo (BR); Mauro Alfredo Soto Oviedo, São Paulo (BR); Fernanda Munhoz Anderle, Campinas (BR); Omar Wandir Renck, São Paulo (BR); José Augusto Esteves Viveiro, São Paulo (BR)

(73) Assignee: Braskem S.A., Camaçari (BR)

( * ) Notice: Subject to any disclaimer, the term of this patent is extended or adjusted under 35 U.S.C. 154(b) by 121 days.

(21) Appl. No.: 17/839,263

(22) Filed: Jun. 13, 2022

(65) Prior Publication Data

US 2022/0306846 A1    Sep. 29, 2022

Related U.S. Application Data

(60) Division of application No. 16/385,918, filed on Apr. 16, 2019, now abandoned, which is a continuation of application No. PCT/IB2019/020007, filed on Apr. 12, 2019.

(60) Provisional application No. 62/658,283, filed on Apr. 16, 2018.

(51) Int. Cl.
| | |
|---|---|
| *C08L 23/08* | (2006.01) |
| *C07C 1/24* | (2006.01) |
| *C08K 5/00* | (2006.01) |
| *C08L 83/04* | (2006.01) |

(52) U.S. Cl.
CPC ......... *C08L 23/0853* (2013.01); *C07C 1/24* (2013.01); *C08K 5/0016* (2013.01); *C08L 23/0807* (2013.01); *C08L 83/04* (2013.01); *C08L 2205/025* (2013.01)

(58) Field of Classification Search
CPC ....... C08L 23/0853; C08L 23/16; C08L 23/22
See application file for complete search history.

(56) References Cited

U.S. PATENT DOCUMENTS

| | | | |
|---|---|---|---|
| 2011/0152454 A1 | 6/2011 | Devisme et al. | |
| 2011/0287204 A1 * | 11/2011 | Devisme ............... | C08F 210/02 428/36.9 |

FOREIGN PATENT DOCUMENTS

| | | | | |
|---|---|---|---|---|
| CA | 2489197 A1 * | 6/2006 | ............ | C08F 218/08 |
| CN | 103205054 A | 7/2013 | | |
| WO | WO-2013053189 A1 * | 4/2013 | ............ | A43B 13/02 |
| WO | WO 2014/053037 * | 4/2014 | | |
| WO | 2019111047 A1 | 6/2019 | | |

OTHER PUBLICATIONS

Machine translation of WO 2014/053037 (no date).*
Machine translation of WO 2013/053189 (no date).*
Office Action issued in corresponding Japanese Patent Application No. 2022-187445, dated Jan. 9, 2024 (20 pages).

* cited by examiner

*Primary Examiner* — Marc S Zimmer
(74) *Attorney, Agent, or Firm* — Osha Bergman Watanabe & Burton LLP (57) ABSTRACT

A polymer composition may include an elastomeric ethylene-vinyl acetate, in which at least a portion of ethylene from the elastomeric ethylene-vinyl acetate is obtained from a renewable source of carbon. A curable polymer composition, an expandable polymer composition, articles, cured articles, and expanded articles may include or be formed from such polymer composition. A process for producing a polymer composition may include polymerizing ethylene at least partially obtained from a renewable source of carbon with vinyl acetate to produce an ethylene vinyl acetate copolymer; and mixing the ethylene-vinyl acetate copolymer with an elastomeric polyolefin to produce an elastomeric ethylene-vinyl acetate.

19 Claims, 2 Drawing Sheets

BIO-BASED ELASTOMERIC EVA COMPOSITIONS AND ARTICLES AND METHODS THEREOF

BACKGROUND

Commercial rubber compositions may be formulated with a variety of primary and secondary polymers and various additives to tune performance based on the final application. For example, rubber compositions that are normally used in the footwear market require a large number of raw materials in order to achieve the attributes necessary for the application, leading to the production of complex and specialized mixtures.

In addition to complex formulations containing a number of additives, curing and vulcanization may create further constraints, limiting the ability to change formulations or reuse rubbers for different applications. The processing difficulty with traditional rubber bases such as SBR (styrene-butadiene rubber), natural rubber and/or blends of different synthetic or natural rubbers, has motivated the search for alternative base materials having similar or improved properties, such as low abrasion, soft touch and lightness, and a reduced number of formulation components

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a polymer composition that includes an elastomeric ethylene-vinyl acetate, in which at least a portion of ethylene from the elastomeric ethylene-vinyl acetate is obtained from a renewable source of carbon.

In another aspect, embodiments disclosed herein relate to an article that may be prepared from a polymer composition that includes an elastomeric ethylene-vinyl acetate, in which at least a portion of ethylene from the elastomeric ethylene-vinyl acetate is obtained from a renewable source of carbon.

In another aspect, embodiments disclosed herein relate to a curable a polymer composition that includes an elastomeric ethylene-vinyl acetate, in which at least a portion of ethylene from the elastomeric ethylene-vinyl acetate is obtained from a renewable source of carbon, and at least a peroxide agent.

In yet another aspect, embodiments disclosed herein relate to a cured article prepared from the curable polymer composition that includes an elastomeric ethylene-vinyl acetate, in which at least a portion of ethylene from the elastomeric ethylene-vinyl acetate is obtained from a renewable source of carbon, and at least a peroxide agent.

In another aspect, embodiments disclosed herein relate to an expandable polymer composition that includes an elastomeric ethylene-vinyl acetate, in which at least a portion of ethylene from the elastomeric ethylene-vinyl acetate is obtained from a renewable source of carbon, and at least a blowing agent and a peroxide agent.

In another aspect, embodiments disclosed herein relate to an expanded article prepared from the expandable polymer composition that includes an elastomeric ethylene-vinyl acetate, in which at least a portion of ethylene from the elastomeric ethylene-vinyl acetate is obtained from a renewable source of carbon, and at least a blowing agent and a peroxide agent.

In yet another aspect, embodiments disclosed herein relate to a process for producing a polymer composition that includes polymerizing ethylene at least partially obtained from a renewable source of carbon with vinyl acetate to produce an ethylene vinyl acetate copolymer; and mixing the ethylene-vinyl acetate copolymer with an elastomeric polyolefin to produce an elastomeric ethylene-vinyl acetate.

In yet another aspect, embodiments disclosed herein relate to a process for producing a polymer composition that includes fermenting a renewable source of carbon to produce ethanol; dehydration of ethanol to produce ethylene; polymerizing ethylene and vinyl acetate to produce an ethylene vinyl acetate copolymer; and mixing the ethylene-vinyl acetate copolymer with an elastomeric polyolefin to produce an elastomeric ethylene-vinyl acetate.

Other aspects and advantages of the claimed subject matter will be apparent from the following description and the appended claims.

DETAILED DESCRIPTION

In one aspect, embodiments disclosed herein relate to rubber compositions containing elastomeric ethylene vinyl acetate (EVA) copolymers that have at least a portion of the ethylene thereof that is obtained from a renewable source of carbon, such as a plant-based material, i.e., forming a bio-based elastomeric ethylene vinyl acetate copolymer.

Polymer compositions in accordance with the present disclosure may be used for the partial or total replacement of rubbers such as styrene-butadiene rubber to prepare expanded and non-expanded articles in applications including shoe sole components, monobloc expanded soles for sandals or flip-flops, and the like, while retaining the required technical requirements demanded by these applications.

Polymer compositions in accordance with the present disclosure may include the reaction products obtained from a mixture of: an elastomeric EVA composition; and one or more of filler, blowing agent, curing agent, or blowing accelerator. The elastomeric EVA may include, for example, a bio-based ethylene vinyl acetate copolymer, an ethylene-alpha olefin copolymer and rubber. Each of the components are discussed in turn as follows EVA is a copolymer of the polyolefin family of elastomers formed by the sequence of random units derived from the polymerization of ethylene and vinyl acetate at high temperature and pressure. EVA copolymers provide materials that can be processed like other thermoplastics, but may offer a rubbery character having softness and elasticity. The use of products derived from natural sources, as opposed to those obtained from fossil sources, has increasingly been widely preferred alternative, as an effective means of reducing the atmospheric carbon dioxide concentration increase, therefore effectively limiting the expansion of the greenhouse effect. Products obtained from natural raw materials have a difference, relative to fossil sourced products, in their renewable carbon content. This renewable carbon content can be certified by the methodology described in the technical ASTM D 6866-18 Norm, "Standard Test Methods for Determining the Biobased Content of Solid, Liquid, and Gaseous Samples Using Radiocarbon Analysis". Products obtained from renewable natural raw materials have the additional property of being able to be incinerated at the end of their life cycle and only produce $CO_2$ of a non-fossil origin. Further, while particular embodiments of the present disclosure may be directed to use of bio-based EVA copolymers in the production of the elastomeric EVA compositions, it is also understood that one or more other components may also be formed from renewable sources. Thus, while some of the below discussion is directed to the amount of bio-based carbon in an EVA copolymer, in one or more embodiments, the elastomeric EVA composition may exhibit a bio-based carbon content, as determined by ASTM D6866-18 Method B of at least 5%. Further, other embodiments may include at least 10%, 20%, 40%, 50%, 60%, 80%, or 90% bio-based carbon. Such bio-based carbon may be entirely contributed by the EVA copolymer or may also be contributed by other components as well.

Elastomeric EVA Composition

Polymeric compositions in accordance with one or more embodiments of the present disclosure may include an elastomeric ethylene vinyl acetate (EVA) composition may be prepared from of (A) a bio-based EVA copolymer, (B) ethylene alpha-olefin copolymer, (C) polyorganosiloxane, (D) plasticizer, and (E) rubber, that are crosslinked in some embodiments by a (F) crosslinking agent. Elastomeric EVA compositions are prepared as disclosed in the Brazilian patent BR102012025160-4, and U.S. Patent Application No. 62/594,307, both of which are incorporated herein in their entirety. The major components of the elastomer composition of the present disclosure as well as their respective properties are detailed below.

(A) EVA Copolymer

Elastomeric EVA compositions in accordance may incorporate one or more ethylene-vinyl acetate (EVA) copolymers prepared by the copolymerization of ethylene and vinyl acetate. In some embodiments, the EVA copolymer can be derived from fossil or renewable sources such as biobased EVA. Biobased EVA is an EVA wherein at least one of ethylene and/or vinyl acetate monomers are derived from renewable sources, such as ethylene derived from biobased ethanol.

Polymer compositions in accordance with the present disclosure may include an EVA copolymer, wherein the percent by weight of ethylene in the EVA polymer ranges from a lower limit selected from one of 60 wt %, 66 wt %, and 72 wt %, to an upper limit selected from one of 82 wt %, 88 wt %, 92 wt %, and 95 wt %, where any lower limit may be paired with any upper limit. Further, of this total amount of ethylene, it is understood that at least a portion of that ethylene is based on a renewable carbon source.

Polymer compositions in accordance with the present disclosure may include EVA copolymers incorporating various ratios of ethylene and vinyl acetate. Polymer compositions in accordance with the present disclosure may include an EVA copolymer, wherein the percent by weight of vinyl acetate in the copolymer, as determined by ASTM D5594, ranges from a lower limit selected from one of 5 wt %, 8 wt %, 12 wt %, and 18 wt % to an upper limit selected from 28 wt %, 33 wt %, and 40 wt %, where any lower limit may be paired with any upper limit. Further, of this total amount of vinyl acetate, it is understood that at least a portion of that vinyl acetate is based on a renewable carbon source.

Specifically, in one or more embodiments, the EVA copolymer exhibits a bio-based carbon content, as determined by ASTM D6866-18 Method B of at least 5%. Further, other embodiments may include at least 10%, 20%, 40%, 50%, 60%, 80%, or 100% bio-based carbon. As mentioned above, the total bio-based or renewable carbon in the EVA polymer may be contributed from a bio-based ethylene and/or a bio-based vinyl acetate. Each of these are described in turn.

For example, in one or more embodiments, the renewable source of carbon is one or more plant materials selected from the group consisting of sugar cane and sugar beet, maple, date palm, sugar palm, sorghum, American agave, corn, wheat, barley, sorghum, rice, potato, cassava, sweet potato, algae, fruit, materials comprising cellulose, wine, materials comprising hemicelluloses, materials comprising lignin, wood, straw, sugarcane bagasse, sugarcane leaves, corn stover, wood residues, paper, and combinations thereof.

In one or more embodiments, the bio-based ethylene may be obtained by fermenting a renewable source of carbon to produce ethanol, which may be subsequently dehydrated to produce ethylene. Further, it is also understood that the fermenting produces, in addition to the ethanol, byproducts of higher alcohols. If the higher alcohol byproducts are present during the dehydration, then higher alkene impurities may be formed alongside the ethanol. Thus, in one or more embodiments, the ethanol may be purified prior to dehydration to remove the higher alcohol byproducts while in other embodiments, the ethylene may be purified to remove the higher alkene impurities after dehydration.

Thus, biologically sourced ethanol, known as bio-ethanol, is obtained by the fermentation of sugars derived from cultures such as that of sugar cane and beets, or from hydrolyzed starch, which is, in turn, associated with other cultures such as corn. It is also envisioned that the bio-based ethylene may be obtained from hydrolysis based products from cellulose and hemi-cellulose, which can be found in many agricultural by-products, such as straw and sugar cane husks. This fermentation is carried out in the presence of varied microorganisms, the most important of such being the yeast *Saccharomyces cerevisiae*. The ethanol resulting therefrom may be converted into ethylene by means of a catalytic reaction at temperatures usually above 300° C. A large variety of catalysts can be used for this purpose, such as high specific surface area gamma-alumina. Other examples include the teachings described in U.S. Pat. Nos. 9,181,143 and 4,396,789, which are herein incorporated by reference in their entirety.

Bio-based vinyl acetate, on the other hand, may also be used in one of more embodiments of the EVA copolymer of the present disclosure. Bio-based vinyl acetate may be produced by producing acetic acid by oxidation of ethanol (which may be formed as described above) followed by reaction of ethylene and acetic acid to acyloxylate the ethylene and arrive at vinyl acetate. Further, it is understood that the ethylene reacted with the acetic acid may also be formed from a renewable source as described above.

Figure 1:
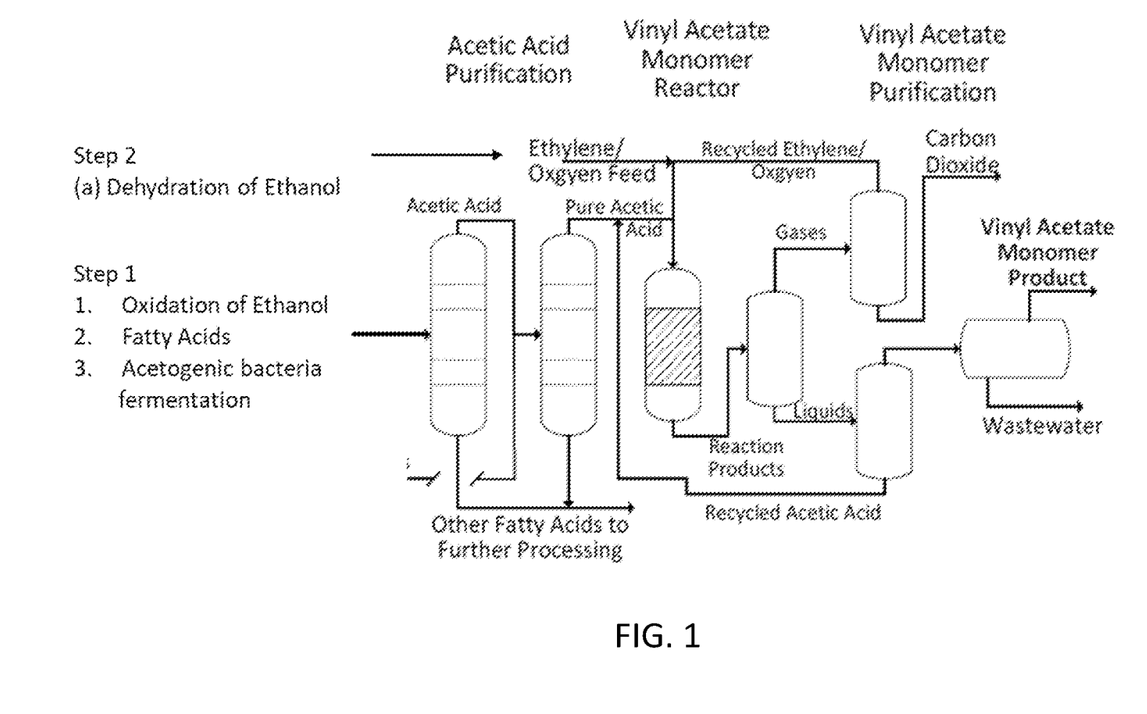
FIG. 1 is an exemplary route for the production of bio-based vinyl acetate according to one or more embodiments of the present disclosure.

An exemplary route of obtaining a bio-based vinyl acetate is shown in FIG. 1. As shown, initially, a fermentation of a renewable starting material, including those described above, and optional purification, in order to produce at least one alcohol (either ethanol or a mixture of alcohols including ethanol). The alcohol may be separated into two parts, where the first part is introduced into a first reactor and the second part may be introduced into a second reactor. In the first reactor, the alcohol may be dehydrated in order to produce an alkene (ethylene or a mixture of alkenes including ethylene, depending on whether a purification followed the fermentation) followed by optional purification to obtain ethylene. One of ordinary skill in the art may appreciate that if the purification occurs prior to dehydration, then it need not occur after dehydration, and vice versa. In the second reactor, the alcohol may be oxidized in order to obtain acetic acid, which may optionally be purified. In a third reactor, the ethylene produced in the first reactor and the acetic acid produced in the second reactor may be combined and reacted to acyloxylate the ethylene and form vinyl acetate, which may be subsequently isolated and optionally purified. Additional details about oxidation of ethanol to form acetic acid may be found in U.S. Pat. No. 5,840,971 and Selective catalytic oxidation of ethanol to acetic acid on dispersed Mo—V—Nb mixed oxides. Li X, Iglesia E. Chemistry. 2007; 13(33):9324-30.

However, the present disclosure is not so limited in terms of the route of forming acetic acid. Rather, it is also envisioned, as indicated on FIG. 1, that acetic acid may be obtained from a fatty acid, as described in The Production of Vinyl Acetate Monomer as a Co-Product from the Non-Catalytic Cracking of Soybean Oil, Benjamin Jones, Michael Linnen, Brian Tande and Wayne Seames, Processes, 2015, 3, 61-9-633. Further, the production of acetic acid from fermentation performed by acetogenic bacteria, as described in *Acetic acid bacteria: A group of bacteria with versatile biotechnological applications*, Saichana N, Matsushita K, Adachi O, Frébort I, Frebortova J. Biotechnol Adv. 2015 Nov. 1; 33(6 Pt 2):1260-71 and Biotechnological applications of acetic acid bacteria. Raspor P, Goranovic D. Crit Rev Biotechnol. 2008; 28(2):101-24. Further, it is also understood that while FIG. 1 is directed to the formation of vinyl acetate, the production of ethylene used to produce vinyl acetate can also be used to form the ethylene that is subsequently reacted with the vinyl acetate to form the EVA copolymer of the present disclosure. Thus, for example, the amount of ethanol that is fed to the first and second reactors, respectively, may be vary depending on the relative amounts of ethylene and vinyl acetate being polymerized.

Polymer compositions in accordance with the present disclosure may include an EVA copolymer, wherein the number average molecular weight (Mn) in kilodaltons (kDa) of the EVA copolymer ranges from a lower limit selected from one of 5 kDa, 10 kDa, 20 kDa and 25 kDa to an upper limit selected from one of 30 kDa, 35 kDa, 40 kDa and 50 kDa, where any lower limit may be paired with any upper limit.

Polymer compositions in accordance with the present disclosure may include an EVA copolymer, wherein the weight average molecular weight (Mw) in kilodaltons (kDa) of the EVA copolymer ranges from a lower limit selected from one of 25 kDa, 50 kDa, 70 kDa, 90 kDa and 110 kDa to an upper limit selected from one of 120 kDa, 140 kDa, 150 kDa and 180 kDa, where any lower limit may be paired with any upper limit.

Polymer compositions in accordance with the present disclosure may include an EVA copolymer, wherein the dispersity (Mw/Mn) of the EVA copolymer ranges from a lower limit selected from one of 1.0, 1.5, 3.0 and 4.0 to an upper limit selected from one of 5.0, 6.0, 7.0 and 8.0, where any lower limit may be paired with any upper limit.

The molecular weight properties may be measured by GPC (Gel Permeation Chromatography) experiments. Such experiments may be coupled with triple detection, such as with an infrared detector IRS and a four-bridge capillary viscometer (PolymerChar) and an eight-angle light scattering detector (Wyatt). A set of 4 mixed bed, 13 μm columns (Tosoh) may be used at a temperature of 140° C. The experiments may use a concentration of 1 mg/mL, a flow rate of 1 mL/min, a dissolution temperature and time of 160° C. and 90 minutes, respectively, an injection volume of 200 μL, and a solvent of trichlorium benzene stabilized with 100 ppm of BHT.

Elastomeric EVA compositions in accordance with the present disclosure may contain an ethylene vinyl acetate copolymer at a percent by weight (wt %) of the composition that ranges from a lower limit of 20 wt %, 30 wt %, 40 wt %, or 50 wt %, to an upper limit of 60 wt %, 70 wt %, 80 wt %, or 90 wt %, where any lower limit may be paired with any upper limit.

(B) Ethylene Alpha-Olefin Copolymer

Elastomeric EVA compositions in accordance may incorporate one or more copolymers prepared from the polymerization of ethylene and a C3 to C20 alpha-olefin.

Ethylene alpha-olefin copolymer in accordance with the present disclosure may have a hardness determined in accordance with ASTM D2240 in a range having a lower limit selected from any of 10 Shore A, 15 Shore A, and 20 Shore A, to an upper limit selected from any of 70 Shore A, 75 Shore A, and 80 Shore A, where any lower limit may be paired with any upper limit.

Ethylene alpha-olefin copolymer in accordance with the present disclosure may have a density determined according to ASTM D792 in a range having a lower limit selected from any of 0.80 g/cm$^3$, 0.85 g/cm$^3$, and 0.88 g/cm$^3$, to an upper limit selected from any of 0.89 g/cm$^3$, 0.90 g/cm$^3$, and 0.95 g/cm$^3$, where any lower limit may be paired with any upper limit.

Ethylene alpha-olefin copolymer in accordance with the present disclosure may have a melt flow index (MFI) at 190° C. and 2.16 kg as determined according to ASTM D1238 in a range having a lower limit selected from any of 0.01 g/10 min, 0.05 g/10 min, and 0.1 g/10 min, 0.5 g/10 min, 1 g/10 min, 5 g/10 min and 10 g/10 min to an upper limit selected from any of 70 g/10 min, 75 g/10 min, and 100 g/10 min, where any lower limit may be paired with any upper limit.

Elastomeric EVA compositions in accordance with the present disclosure may contain an ethylene alpha-olefin copolymer at a percent by weight (wt %) of the composition that ranges from a lower limit of 5 wt % or 10 wt %, to an upper limit of 30 wt % or 60 wt %, where any lower limit may be paired with any upper limit.

(C) Polyorganosiloxane

Elastomeric EVA compositions in accordance with the present disclosure may incorporate a polyorganosiloxane. In one or more embodiments, suitable polyorganosiloxanes include a linear chain, branched, or three-dimensional structure, wherein the side groups can include one or more of methyl, ethyl, propyl groups, vinyl, phenyl, hydrogen, amino, epoxy, or halogen substituents. The terminal groups of the polyorganosiloxane may include hydroxyl groups, alkoxy groups, trimethylsilyl, dimethyldiphenylsilyl, and the like. Polyorganosiloxanes in accordance with the present disclosure may include one or more of dimethylpolysiloxane, methylpolysiloxane, and the like.

Elastomeric EVA compositions in accordance with the present disclosure may contain a polyorganosiloxane having a viscosity measured at 25° C. that ranges from a lower limit of 20 cP or 40 cP, to an upper limit of 700,000 cP or 900,000 cP, where any lower limit may be paired with any upper limit.

Elastomeric EVA compositions in accordance with the present disclosure may contain a polyorganosiloxane at a percent by weight (wt %) of the composition that ranges from a lower limit of 0.1 wt % or 0.5 wt %, to an upper limit of 5 wt % or 10 wt %, where any lower limit may be paired with any upper limit.

(D) Plasticizer

Elastomeric EVA compositions in accordance may incorporate a plasticizer to improve the processability and adjust the hardness of the elastomeric EVA. Plasticizers in accordance with the present disclosure may include one or more of bis(2-ethylhexyl) phthalate (DEHP), di-isononyl phthalate (DINP), bis (n-butyl) phthalate (DNBP), butyl benzyl phthalate (BZP), di-isodecyl phthalate (DIDP), di-n-octyl phthalate (DOP or DNOP), di-o-octyl phthalate (DIOP), diethyl phthalate (DEP), di-isobutyl phthalate (DIBP), di-n-hexyl phthalate, tri-methyl trimellitate (TMTM), tri-(2-ethylhexyl) trimellitate (TEHTM-MG), tri-(n-octyl, n-decyl) trimellitate, tri-(heptyl, nonyl) trimellitate, n-octyl trimellitate, bis (2-ethylhexyl) adipate (DEHA), dimethyl adipate (DMD), mono-methyl adipate (MMAD), dioctyl adipate (DOA)), dibutyl sebacate (DBS), polyesters of adipic acid such as VIERNOL, dibutyl maleate (DBM), di-isobutyl maleate (DIBM), benzoates, epoxidized soybean oils, n-ethyl toluene sulfonamide, n-(2-hydroxypropyl) benzene sulfonamide, n-(n-butyl) benzene sulfonamide, tricresyl phosphate (TCP), tributyl phosphate (TBP), glycols/polyesters, triethylene glycol dihexanoate, 3gh), tetraethylene glycol di-heptanoate, polybutene, acetylated monoglycerides; alkyl citrates, triethyl citrate (TEC), acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trihexyl o-butyryl citrate, trimethyl citrate, alkyl sulfonic acid phenyl ester, 2-cyclohexane dicarboxylic acid di-isononyl ester, nitroglycerin, butanetriol trinitrate, dinitrotoluene, trimethylolethane trinitrate, diethylene glycol dinitrate, triethylene glycol dinitrate, bis (2,2-dinitropropyl) formal, bis (2,2-dinitropropyl) acetal, 2,2,2-trinitroethyl 2-nitroxyethyl ether, mineral oils, among other plasticizers and polymeric plasticizers.

Elastomeric EVA compositions in accordance with the present disclosure may contain a plasticizer at a percent by weight (wt %) of the composition that ranges from a lower limit of 0.5 wt % or 2 wt %, to an upper limit of 10 wt % or 20 wt %, where any lower limit may be paired with any upper limit.

(E) Rubber

Elastomeric EVA compositions in accordance may incorporate a rubber component to increase the rubbery touch and increase the coefficient of friction, depending on the end application. Rubbers in accordance with the present disclosure may include one or more of natural rubber, polyisoprene (IR), styrene and butadiene rubber (SBR), polybutadiene, nitrile rubber (NBR); polyolefin rubbers such as ethylene-propylene rubbers (EPDM, EPM), and the like, acrylic rubbers, halogen rubbers such as halogenated butyl rubbers including brominated butyl rubber and chlorinated butyl rubber, brominated isobutylene, polychloroprene, and the like; silicone rubbers such as methylvinyl silicone rubber, dimethyl silicone rubber, and the like, sulfur-containing rubbers such as polysulfidic rubber; fluorinated rubbers; thermoplastic rubbers such as elastomers based on styrene, butadiene, isoprene, ethylene and propylene, styrene-isoprene-styrene (SIS), styrene-ethylene-butylene-styrene (SEBS), styrene-butylene-styrene (SBS), and the like, ester-based elastomers, elastomeric polyurethane, elastomeric polyamide, and the like.

Rubbers in accordance with the present disclosure may have a hardness determined in accordance with ASTM D2240 in a range having a lower limit selected from any of 10 Shore A, 15 Shore A, and 20 Shore A, to an upper limit selected from any of 45 Shore A, 50 Shore A, and 55 Shore A, where any lower limit may be paired with any upper limit.

Elastomeric EVA compositions in accordance with the present disclosure may contain a rubber at a percent by weight (wt %) of the composition that ranges from a lower limit of 0.5 wt % or 1 wt %, to an upper limit of 20 wt % or 40 wt %, where any lower limit may be paired with any upper limit.

In one or more embodiments, the elastomeric EVA composition may have a melt flow index (MFI) at 190° C. and 2.16 kg as determined according to ASTM D1238 in a range having a lower limit selected from any of 1 g/10 min, 2 g/10 min, 3 g/10 min, and 4 g/10 min, to an upper limit selected from any of 10 g/10 min, 15 g/10 min, 20 g/10 min, 25 g/10 min, and, where any lower limit may be paired with any upper limit, where any lower limit may be paired with any upper limit.

In one or more embodiments, the elastomeric EVA composition may have a density determined according to ASTM D792 in a range having a lower limit selected from any of 0.92 g/cm$^3$, 0.93 g/cm$^3$, and 0.94 g/cm$^3$, to an upper limit selected from any of 0.94 g/cm$^3$, 0.95 g/cm$^3$, and 0.96 g/cm$^3$, where any lower limit may be paired with any upper limit.

In one or more embodiments, the elastomeric EVA composition exhibits a Shore A hardness as determined by ASTM D2240 that may range from a lower limit of any of 40, 50, or 60 to an upper limit of 70, 80, or 90 Shore A, where any lower limit may be paired with any upper limit.

Filler

Polymeric compositions in accordance with the present disclosure may be loaded with fillers that may include carbon black, silica powder, calcium carbonate, talc, titanium dioxide, clay, polyhedral oligomeric silsesquioxane (POSS), metal oxide particles and nanoparticles, inorganic salt particles and nanoparticles, recycled EVA, and mixtures thereof.

As defined herein, recycled EVA may be derived from regrind materials that have undergone at least one processing method such as molding or extrusion and the subsequent sprue, runners, flash, rejected parts, and the like, are ground or chopped.

In one or more embodiments, polymeric compositions in accordance with the present disclosure one or more fillers at a parts per hundred of resin (phr) that ranges from a lower limit selected from one of 5 phr, 10 phr, 15 phr, 20 phr, 25 phr, 30 phr, 35 phr, 40 pht, and 55 phr to an upper limit selected from one of 60 phr, 80 phr, 100 phr, 120 phr, 140 phr, 160 phr, 180 phr, 200 phr, and 220 phr where any lower limit can be used with any upper limit.

Peroxide Agent

Polymer compositions in accordance with the present disclosure may include one or more peroxide agents capable of generating free radicals during polymer processing. For example, peroxide agents may be combined with an EVA resin while reacting the polymer such as during polymerization and/or curing. In one or more embodiments, peroxide agents may include bifunctional peroxides such as benzoyl peroxide; dicumyl peroxide; di-tert-butyl peroxide; 00-Tert-amyl-0-2-ethylhexyl monoperoxycarbonate; tert-butyl cumyl peroxide; tert-butyl 3,5,5-trimethylhexanoate peroxide; tert-butyl peroxybenzoate; 2-ethylhexyl carbonate tert-butyl peroxide; 2,5-dimethyl-2,5-di (tert-butylperoxide) hexane; 1,1-di (tert-butylperoxide)-3,3,5-trimethylcyclohexane; 2,5-dimethyl-2,5-di(tert-butylperoxide) hexyne-3; 3,3,5,7,7-pentamethyl-1,2,4-trioxepane; butyl 4,4-di (tert-butylperoxide) valerate; di (2,4-dichlorobenzoyl) peroxide; di(4-methylbenzoyl) peroxide; peroxide di(tert-butylperoxyisopropyl) benzene; and the like.

Peroxide agents may also include benzoyl peroxide, 2,5-di(cumylperoxy)-2,5-dimethyl hexane, 2,5-di(cumylperoxy)-2,5-dimethyl hexyne-3,4-methyl-4-(t-butylperoxy)-2-pentanol, butyl-peroxy-2-ethyl-hexanoate, tert-butyl peroxypivalate, tertiary butyl peroxyneodecanoate, t-butyl-peroxy-benzoate, t-butyl-peroxy-2-ethyl-hexanoate, 4-methyl-4-(t-amylperoxy)-2-pentanol, 4-methyl-4-(cumylperoxy)-2-pentanol, 4-methyl-4-(t-butylperoxy)-2-pentanone, 4-methyl-4-(t-amylperoxy)-2-pentanone, 4-methyl-4-(cumylperoxy)-2-pentanone, 2,5-dimethyl-2,5-di(t-butylperoxy)hexane, 2,5-dimethyl-2,5-di(t-amylperoxy) hexane, 2,5-dimethyl-2,5-di(t-butylperoxy)hexyne-3, 2,5-dimethyl-2,5-di(t-amylperoxy)hexyne-3, 2,5-dimethyl-2-t-butylperoxy-5-hydroperoxyhexane, 2,5-dimethyl-2-cumylperoxy-5-hydroperoxy hexane, 2,5-dimethyl-2-t-amylperoxy-5-hydroperoxyhexane, m/p-alpha, alpha-di[(t-butylperoxy)isopropyl]benzene, 1,3,5-tris(t-butylperoxyisopropyl)benzene, 1,3,5-tris(t-amylperoxyisopropyl)benzene, 1,3,5-tris (cumylperoxyisopropyl)benzene, di[1,3-dimethyl-3-(t-butylperoxy)butyl]carbonate, di[1,3-dimethyl-3-(t-amylperoxy)butyl]carbonate, di[1,3-dimethyl-3-(cumylperoxy)butyl]carbonate, di-t-amyl peroxide, t-amyl cumyl peroxide, t-butyl-isopropenylcumyl peroxide, 2,4,6-tri(butylperoxy)-s-triazine, 1,3,5-tri[1-(t-butylperoxy)-1-methylethyl]benzene, 1,3,5-tri-[(t-butylperoxy)-isopropyl] benzene, 1,3-dimethyl-3-(t-butylperoxy)butanol, 1,3-dimethyl-3-(t-amylperoxy)butanol, di(2-phenoxyethyl) peroxydicarbonate, di(4-t-butylcyclohexyl) peroxydicarbonate, dimyristyl peroxydicarbonate, dibenzyl peroxydicarbonate, di(isobornyl)peroxydicarbonate, 3-cumylperoxy-1,3-dimethylbutyl methacrylate, 3-t-butylperoxy-1,3-dimethylbutyl methacrylate, 3-t-amylperoxy-1,3-dimethylbutyl methacrylate, tri(1,3-dimethyl-3-t-butylperoxy butyloxy)vinyl silane, 1,3-dimethyl-3-(t-butylperoxy)butyl N-[1-{3-(1-methylethenyl)-phenyl) 1-methylethyl]carbamate, 1,3-dimethyl-3-(t-amylperoxy)butyl N-[1-{3(1-methylethenyl)-phenyl}-1-methylethyl]carbamate, 1,3-dimethyl-3-(cumylperoxy))butyl N-[1-{3-(1-methylethenyl)-phenyl}-1-methylethyl]carbamate, 1,1-di(t-butylperoxy)-3,3,5-trimethylcyclohexane, 1,1-di(t-butylperoxy)cyclohexane, n-butyl 4,4-di(t-amylperoxy)valerate, ethyl 3,3-di(t-butylperoxy)butyrate, 2,2-di(t-amylperoxy)propane, 3,6,6,9,9-pentamethyl-3-ethoxycabonylmethyl-1,2,4,5-tetraoxacyclononane, n-buty 1-4,4-bis(t-butylperoxy)valerate, ethyl-3,3-di(t-amylperoxy)butyrate, benzoyl peroxide, OO-t-butyl-O-hydrogen-monoperoxy-succinate, OO-t-amyl-O-hydrogen-monoperoxy-succinate, 3,6,9, triethyl-3,6,9-trimethyl-1,4,7-triperoxynonane (or methyl ethyl ketone peroxide cyclic trimer), methyl ethyl ketone peroxide cyclic dimer, 3,3,6,6, 9,9-hexamethyl-1,2,4,5-tetraoxacyclononane, 2,5-dimethyl-2,5-di(benzoylperoxy)hexane, t-butyl perbenzoate, t-butylperoxy acetate, t-butylperoxy-2-ethyl hexanoate, t-amyl perbenzoate, t-amyl peroxy acetate, t-butyl peroxy isobutyrate, 3-hydroxy-1,1-dimethyl t-butyl peroxy-2-ethyl hexanoate, OO-t-amyl-O-hydrogen-monoperoxy succinate, OO-t-butyl-O-hydrogen-monoperoxy succinate, di-t-butyl diperoxyphthalate, t-butylperoxy (3,3,5-trimethylhexanoate), 1,4-bis(t-butylperoxycarbo)cyclohexane, t-butylperoxy-3,5,5-trimethylhexanoate, t-butyl-peroxy-(cis-3-carboxy)propionate, allyl 3-methyl-3-t-butylperoxy butyrate, 004-butyl-O-isopropylmonoperoxy carbonate, OO-t-butyl-O-(2-ethyl hexyl)monoperoxy carbonate, 1,1,1-tris[2-O-butylperoxy-carbonyloxy)ethoxymethyl]propane, 1,1,1-tris [2-O-amylperoxy-carbonyloxy)ethoxymethyl]propane, 1,1, 1-tris[2-(cumylperoxy-cabonyloxy)ethoxymethyl]propane, OO-t-amyl-O-isopropylmonoperoxy carbonate, di(4-methylbenzoyl)peroxide, di(3-methylbenzoyl)peroxide, di(2-methylbenzoyl)peroxide, didecanoyl peroxide, dilauroyl peroxide, 2,4-dibromo-benzoyl peroxide, succinic acid peroxide, dibenzoyl peroxide, di(2,4-dichloro-benzoyl)peroxide, and combinations thereof.

In one or more embodiments, polymeric compositions in accordance with the present disclosure may contain one or more peroxide agents at a parts per hundred of resin (phr) of that ranges from a lower limit selected from one of 0.5 phr, 0.75 phr, 1 phr, 1.5 phr and 2 phr, to an upper limit selected from one of 2.5 phr, 2.75 phr, 3 phr, 3.5 phr and 4 phr, where any lower limit can be used with any upper limit. Further, it is envisioned that the concentration of the peroxide agent may be more or less depending on the application of the final material.

Crosslinking Co-Agents

It is also envisioned that crosslinking co-agent may be combined in the polymer composition during the curing processes. Crosslinking co-agents create additional reactive sites for crosslinking. Therefore, the degree of polymer crosslinking may be considerably increased from that normally obtained by greater additions of peroxide. Generally co-agents increase the rate of crosslinking. In one or more embodiments, the crosslinking co-agents may include Triallyl isocyanurate (TAIL), trimethylolpropane-tris-methacrylate (TRIM), triallyl cyanurate (TAC) and combinations thereof.

In one or more embodiments, polymeric compositions in accordance with the present disclosure may contain one or more crosslinking co-agent at a parts per hundred resin (phr) that ranges from a lower limit selected from one of 0.01 phr, 0.25 phr, 0.5 phr, 1 phr to an upper limit selected from one of 1.5 phr and 2 phr.

Blowing Agent

Polymeric compositions in accordance with the present disclosure may include one or more blowing agents to produce expanded polymeric compositions and foams. Blowing agents may include solid, liquid, or gaseous blowing agents. In embodiments utilizing solid blowing agents, blowing agents may be combined with a polymer composition as a powder or granulate.

Blowing agents in accordance with the present disclosure include chemical blowing agents that decompose at polymer processing temperatures, releasing the blowing gases such as $N_2$, $CO$, $CO_2$, and the like. Examples of chemical blowing agents may include organic blowing agents, including hydrazines such as toluenesulfonyl hydrazine, hydrazides such as oxydibenzenesulfonyl hydrazide, diphenyl oxide-4, 4'-disulfonic acid hydrazide, and the like, nitrates, azo compounds such as azodicarbonamide, cyanovaleric acid, azobis(isobutyronitrile), and N-nitroso compounds and other nitrogen-based materials, and other compounds known in the art.

Inorganic chemical blowing agents may include carbonates such as sodium hydrogen carbonate (sodium bicarbonate), sodium carbonate, potassium bicarbonate, potassium carbonate, ammonium carbonate, and the like, which may be used alone or combined with weak organic acids such as citric acid, lactic acid, or acetic acid.

In one or more embodiments, polymeric compositions in accordance with the present disclosure may contain one or more blowing agents at a parts per hundred resin (phr) that ranges from a lower limit selected from one of 1 phr, 1.5 phr, 2 phr, 2.5 phr and 3 phr, to an upper limit selected from one of 3.5 phr, 4 phr, 4.5 phr, 5 phr, 5.5 phr and 6 phr, where any lower limit can be used with any upper limit.

Blowing Accelerators

Polymeric compositions in accordance with the present disclosure may include one or more blowing accelerators (also known as kickers) that enhance or initiate the action of a blowing agent by lower the associated activation temperature. For example, blowing accelerators may be used if the selected blowing agent reacts or decomposes at temperatures higher than 170° C., such as 220° C. or more, where the surrounding polymer would be degraded if heated to the activation temperature. Blowing accelerators may include any suitable blowing accelerator capable of activating the selected blowing agent. In one or more embodiments, suitable blowing accelerators may include cadmium salts, cadmium-zinc salts, lead salts, lead-zinc salts, barium salts, barium-zinc (Ba—Zn) salts, zinc oxide, titanium dioxide, triethanolamine, diphenylamine, sulfonated aromatic acids and their salts, and the like.

In one or more embodiments, polymeric compositions in accordance with the present disclosure may contain one or more blowing accelerators at a parts per hundred resin (phr) that ranges from a lower limit selected from one of 0.1 phr, 0.25 phr, 0.5 phr, 1 phr, 2 phr, and 2.5 phr, to an upper limit selected from one of 1.5 phr, 2 phr, 2.5 phr, 3 phr, 3.5 phr, 4 phr, 4.5 phr and 5 phr, where any lower limit can be used with any upper limit.

Additives

Polymer compositions in accordance with the present disclosure may include additives that modify various physical and chemical properties when added to the polymer composition during blending that include one or more polymer additives such as processing aids, lubricants, antistatic agents, clarifying agents, nucleating agents, beta-nucleating agents, slipping agents, antioxidants, compatibilizers, antacids, light stabilizers such as HALS, IR absorbers, whitening agents, inorganic fillers, organic and/or inorganic dyes, anti-blocking agents, processing aids, flame-retardants, plasticizers, biocides, adhesion-promoting agents, metal oxides, mineral fillers, glidants, oils, antioxidants, antiozonants, accelerators, and vulcanizing agents.

Preparation

Polymeric compositions in accordance with the present disclosure may be prepared in any conventional mixture device. In one or more embodiments, polymeric compositions may be prepared by mixture in conventional kneaders, banbury mixers, mixing rollers, twin screw extruders, and the like, in conventional EVA processing conditions and subsequently cured or cured and expanded in conventional expansion processes, such as injection molding or compression molding.

In one or more embodiments, the EVA copolymer in accordance with the present disclosure may be prepared in reactor. Ethylene and vinyl acetate are added in a reactor to polymerize. In some embodiments, the ethylene, vinyl acetate are polymerized by high pressure radical polymerization, wherein peroxide agents act as polymerization initiators. In some embodiments, the ethylene and the vinyl acetate, and the peroxide agents are added at elevated pressure into an autoclave or tubular reactor at a temperature of between 80° C. and 300° C. and a pressure inside the reactor between 500 bar and 3000 bar in some embodiments, and a pressure between 1000 bar and 2600 bar in some embodiments. In other embodiments, the copolymers may be produced by a solution polymerization process.

As mentioned, one or more free-radical producing agents, including any of those described above may be present during the polymerization. Further, it is also understood that upon being mixed with the other components forming the polymer composition, the polymer composition may also be cured for example in the presence of peroxides as well, including those discussed above, and optionally, a crosslinking co-agent. For embodiments which include expanded compositions, discussed below, the expanding and curing may be in the presence of a blowing agent and a peroxide agent, and optionally, a blowing accelerator or crosslinking co-agent. During any of such curing steps, in one or more embodiments, the curing may occur in full or partial presence of oxygen, such as described in WO201694161A1, which is incorporated by reference in its entirety.

Physical Properties

Polymer compositions in accordance with the present disclosure may have good performance as a replacement for rubber materials with acceptable performance at high and low temperatures, with little or no odor, and comparable or lower density to standard rubber formulations. In one or more embodiments, polymer compositions may exhibit high flexibility, suitable hardness, good abrasion resistance, high coefficient of friction, and soft touch. In some embodiments, articles prepared from polymer compositions in accordance with the present disclosure may take the form of expanded or non-expanded polymer structures.

A cured non-expanded article that includes the polymer compositions of the present disclosure may have a density as determined by ASTM D-792 that may range of a lower limit of any of 0.7, 0.8, 0.9, or 1.0 to an upper limit of any of 1.0, 1.1, or 1.2 g/cm$^3$, where any lower limit can be used with any upper limit.

Cured non-expanded articles prepared by the polymer compositions in accordance with the present disclosure may have a hardness as determined by ASTM D2240 within a range having a lower limit selected from one of 40, 50, or 60 Shore A, to an upper limit selected from one of 60, 70, 80, and 90 Shore A, where any lower limit may be paired with any upper limit.

Cured non-expanded articles prepared by the polymer compositions in accordance with the present disclosure may have an abrasion resistance as determined by ISO 4649:2017 measured with a load of 10N within a range having a lower limit selected from one of 10, 20, 40, 80, to an upper limit selected from one of 100 mm$^3$, 150 mm$^3$, 200 mm$^3$, or 250 mm$^3$, where any lower limit may be paired with any upper limit.

Cured non-expanded articles prepared by the polymer compositions in accordance with the present disclosure may have an elongation at break as determined by ASTM D638 that is at least 200%, 250%, or 300%.

Further, as mentioned, it is also envisioned that the elastomeric EVA compositions may be expanded and cured, such as with the described blowing agent and peroxide agent. Expanded articles prepared by the polymer compositions in accordance with the present disclosure may have a density as determined by ASTM D-792 within a range having a lower limit selected from one of 0.05 g/cm$^3$, 0.12 g/cm$^3$, 0.2 g/cm$^3$, 0.25 g/cm$^3$, 0.5 g/cm$^3$, to an upper limit selected from one of 0.4 g/cm$^3$, 0.5 g/cm$^3$, 0.6 g/cm$^3$, 0.65 g/cm$^3$, 0.70 g/cm$^3$, 0.90 g/cm$^3$ where any lower limit may be paired with any upper limit.

Expanded articles prepared by the polymer compositions in accordance with the present disclosure may have an Asker C hardness as determined by ABNT NBR 14455:2015 in the range having a lower limit of any of 20, 30, 40 or 50 Asker C and an upper limit of any 60, 70, 80, or 90 Asker C, where any lower limit can be paired with any upper limit.

Expanded articles prepared by the polymer compositions in accordance with the present disclosure may have a permanent compression set (PCS) as determined by D395: 2016 Method B within a range having a lower limit selected from one of 20%, 30%, 40%, or 50% to an upper limit selected from one of 60%, 70%, 80%, 90%, or 100% where any lower limit may be paired with any upper limit.

Expanded articles prepared by the polymer compositions in accordance with the present disclosure may have a rebound as determined by ABNT NBR 8619:2015 within a range having a lower limit selected from one of 30%, 35%, 40%, 45%, and 50% to an upper limit selected from one of 50%, 60%, 70%, and 80%, where any lower limit may be paired with any upper limit.

Expanded articles prepared by the polymer compositions in accordance with the present disclosure may have a shrinkage at 70° C.*1 h using the PFI method (PFI "Testing and Research Institute for the Shoe Manufacturing Industry" in Pirmesens—Germany) within a range having a lower limit selected from one of 0.1%, 1%, 1.5%, and 5% to an upper limit selected from one of 4%, 5%, 6%, and 7%, where any lower limit may be paired with any upper limit.

The PFI method may be used in the industry for shrinkage measurements and is detailed below:

Equipment:
  oven with forced air circulation
  pachymeter
  ruler for marking of specimens or template
  thickness gauge Sample
  Three specimens of dimensions of at least 100×100 mm should be evaluated of each sample.

Procedure
  The specimens may be conditioned at a temperature of 23±2° C. and a relative humidity of 50±5% for 1 hour. The approximate thickness of the specimens is measured.

Figure 2:
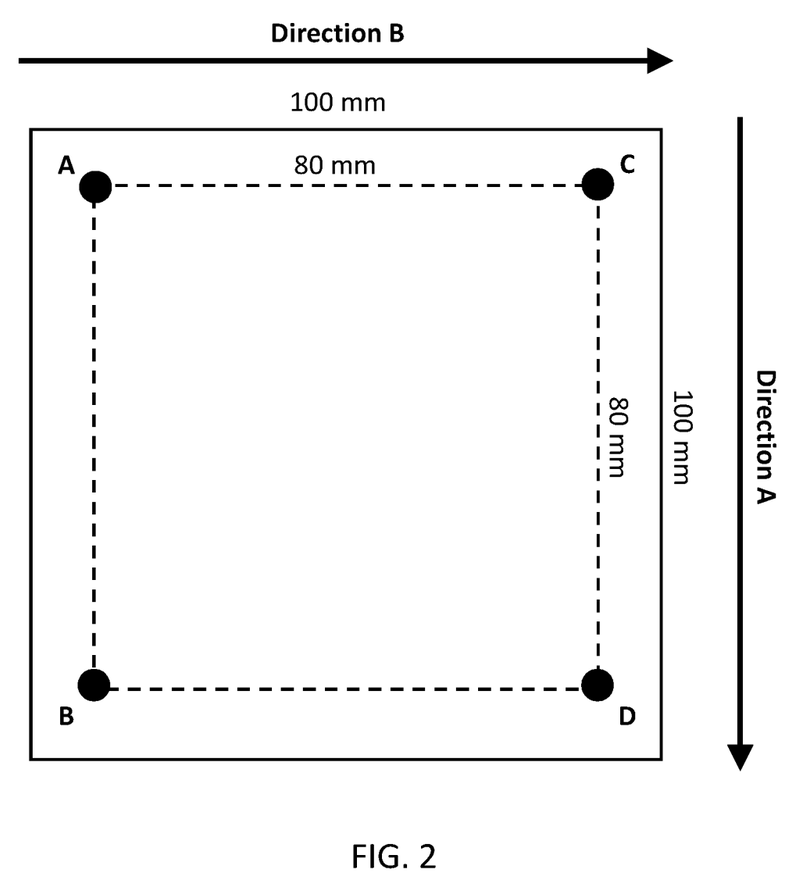
FIG. 2 depicts various points pertinent to the PFI method of determining article shrinkage according to one or more embodiments of the present disclosure.

Using a ruler or template, the points A, B, C and D are marked on each of the specimens as shown in FIG. 2.

The initial length ($C_i$) is measured with a pachymeter, to the nearest 0.01 mm, in direction A (segments A-B and C-D) and in the direction B (segments A-C and B-D).

The specimens are then held at 70° C. for 1 hour in a forced air circulation oven.

After the exposure period, the specimens are removed from the oven and conditioned at a temperature of 23±2° C. and a relative humidity of 50±5% for 60 minutes.

The final length ($C_f$) is measured with a caliper, to the nearest 0.01 mm, in direction A (segments A-B and C-D) and direction B (segments A-C and B-D).

The average initial length ($C_{im}$) is calculated in the A direction as the average of the A-B and C-D segments and in the B direction as the average of the A-C and B-D segments for each of the specimens.

The average final length ($C_{fm}$) is calculated in the A direction as the average of the A-B and C-D segments and the B direction as the average of the A-C and B-D segments for each of the specimens.

Results
  The shrinkage of the expanded EVA is given by the following equation, expressed as a percentage to the nearest 0.1%.

$$\text{Shrinkage \%} = (C_{im} - C_{fm}) \times 100 / C_{im}$$

Where:
  $C_{im}$=initial length average (mm)
  $C_{fm}$=final length average (mm)

The final EVA shrinkage result will be calculated for the directions A and B as the average of the shrinkage values calculated for each specimen.

Note: The PFI recommends acceptable maximum values for shrinkage of expanded materials in directions A and B (FIG. 1):
  3% for materials with a density up to 0.6 g/cm$^3$
  2% for materials with a density above 0.6 g/cm$^3$ Expanded articles prepared by the polymer compositions in accordance with the present disclosure may have an abrasion resistance as determined by ISO 4649 measured with a load of 5N within a range having a lower limit selected from one of 40 mm$^3$, 80 mm$^3$, 120 mm$^3$, 150 mm$^3$, 200 mm$^3$, or 400 mm$^3$, to an upper limit selected from one of 300 mm$^3$, 600 mm$^3$, or 700 mm$^3$, where any lower limit may be paired with any upper limit.

Expanded articles prepared by the polymer composition in accordance with the present disclosure may have an elongation at break as determined by ASTM D638 that is at least 300%, 350%, or 400%.

Applications

In one or more embodiments, polymer compositions can be used in various molding processes, including extrusion molding, injection molding, compression molding, thermoforming, cast film extrusion, blown film extrusion, foaming, extrusion blow-molding, injection blow-molding, ISBM (Injection Stretched Blow-Molding), pultrusion, 3D printing, rotomolding, double expansion process, and the like, to produce manufactured articles.

Polymer compositions in accordance with the present disclosure may also be formulated for a number of polymer articles, including the production of insoles, midsole, soles, hot-melt adhesives, primers, in civil construction as linings, industrial floors, acoustic insulation. Polymeric compositions in accordance with the present disclosure may be formed into articles used for a diverse array of end-uses including shoe soles, midsoles, outsoles, unisoles, insoles, monobloc sandals and flip flops, and full EVA footwear.

Other applications may include seals, hoses, gaskets, foams, foam mattresses, furniture, electro-electronic, automotive, packaging, EVA tires, bras, mats, paperboards, sportive articles, toys, swimming accessories, legs floats, yoga blocks, dumbbell gloves, gym steps, rodo sheets, kimono strips, sandpapers, finger protectors, wall protectors, finger separators, educational games and articles, decorative panels, EVA balls, twisted Hex stools, slippers, pillow, sponges, seats, cycling bib pad, protective covers, carpets, aprons and others.

EXAMPLES

In the following examples, polymer compositions formulations where prepared and assayed to study various physical properties.

Example 1—Production of Biobased Copolymers of Ethylene Vinyl Acetate

A biobased copolymer of ethylene and vinyl acetate according to the present invention was prepared using ethylene obtained from the dehydration of ethanol obtained from sugarcane. Dehydration of ethanol to produce ethylene was conducted in a series of four fixed bed adiabatic reactors connected in series with temperature varying from 350° C. to 480° C. and a pressure of 3 to 10 atm, using an alumina catalyst. The reaction product is subsequently purified by cryogenic distillation and a polymer grade ethylene is obtained.

This copolymer of ethylene and vinyl acetate was produced in a high pressure tubular reactor with 1.110 m in length and 50 mm in diameter. The ethylene is injected at a flow rate of 8.5 tonnes/hour into the reactor and vinyl acetate in injected at a flow rate of 2000 kg/hour. The mixture is compressed in a hypercompressor to 2400 bar and preheated at 130° C. A mixture of tertiary-butyl peroxypivalate/t-Butyl Peroxy-2-ethyl-hexanoate 00-Tert-amyl-0-2-ethylhexyl monoperoxycarbonate was used as initiator. The reaction temperature was varied between 190° C. and 250° C., with a production of 8.5 tonnes/hour of EVA copolymer.

TABLE 1

Biobased EVA obtained according to the present disclosure

| Properties | Unit | Value |
|---|---|---|
| Vinyl acetate content | wt % | 18.7 |
| Melt Index (190° C.@2.16 kg) | g/10 min | 1.95 |
| Density | g/cm$^3$ | 0.941 |
| Hardness | Shore A | 89 |
| VICAT softening temperature | ° C. | 64 |
| Biobased carbon content | % | 88 |

Example 2—Preparation of Elastomeric EVA

In the following example, an elastomeric EVA formed with bio-based EVA in accordance with the present disclosure, and commercially available as SVT2145R from Braskem SA, was tested to determine the properties set forth in Table 2.

TABLE 2

Properties of elastomeric EVA in accordance with the present disclosure

| Properties | Unit | Value |
|---|---|---|
| Vinyl acetate content | wt % | 15 |
| Melt Index (190° C.@2.16 kg) | g/10 min | 1.9 |
| Density | g/cm$^3$ | 0.915 |
| Hardness | Shore A | 79 |
| VICAT softening temperature | ° C. | 43 |
| Biobased carbon content | % | 48 |

Example 3—Preparation of Cured Non-Expanded Articles

In the following example, curable polymeric composition formulations were prepared in a kneader model XSN-5 QUANZHOU YUCHENGSHENG MACHINE CO., LTD at a temperature of 100° C. and subsequently laminated in a cylinder (open-mix) and pressed and cured in a hydraulic press model LPB-100-AQ-EVA from Luxor Indústria de Máquinas Ltda at 175° C. for 7 min to produce plaques of 10×10 cm, which were assayed to study various physical properties. Curable polymeric composition formulations, including also a mixture of biobased elastomeric EVA and biobased EVA, are shown in Table 3.

TABLE 3

Curable non-expanded polymer compositions

| Material | C1 PHR | C2 PHR |
|---|---|---|
| Elastomeric EVA of example 2 | 100 | 50 |
| Biobased EVA produced in example 1 | 0 | 50 |
| Stearic Acid | 1 | 1 |
| Peroxide agent (bis-peroxide 40%) | 2 | 2 |
| Total | 103 | 103 |

Samples were assayed for hardness (Shore A and Shore D), density, abrasion resistance and biobased content, and the results are shown in Table 4.

TABLE 4

Properties of cured non-expanded polymer compositions

| Properties | Unit | C1 | C2 |
|---|---|---|---|
| Hardness Shore D | Shore D | 24 | 31 |
| Hardness Shore A | Shore A | 82 | 84 |
| Density | g/cm$^3$ | 0.898 | 0.931 |
| Abrasion | mm$^3$ | 41 | 28 |
| Biobased carbon content | % | 47 | 68 |

Example 4—Preparation of Expanded Articles

In the following example, expandable polymeric composition formulations were prepared in a kneader model XSN-5 QUANZHOU YUCHENGSHENG MACHINE CO., LTD at a temperature of 105° C. and subsequently laminated in a cylinder (open-mix) and pressed and cured in a hydraulic press model LPB-100-AQ-EVA from Luxor Indústria de Máquinas Ltda at 175° C. for 7 min and expanded at different expansion rates to produce plaques, which were assayed to study various physical properties. Expandable polymeric composition formulations are shown in Table 5.

TABLE 5

Expandable polymer compositions

| Material | C3 PHR | C4 PHR | C5 PHR | C6 PHR |
|---|---|---|---|---|
| Biobased elastomeric EVA of example 2 | 100 | 100 | 100 | 50 |
| Biobased EVA produced in example 1 | 0 | 0 | 0 | 50 |
| Calcium Carbonate | 10 | 10 | 10 | 10 |
| Zinc Oxide | 2 | 2 | 2 | 2 |
| Stearic Acid | 1 | 1 | 1 | 1 |
| Blowing Agent (azodicarbonamide) | 1.3 | 2.2 | 1.6 | 3 |
| Peroxide agent (bis-peroxide 40%) | 2 | 2 | 2 | 2 |
| Total | 116.3 | 117.2 | 116.6 | 118 |

Samples were assayed for hardness (Shore A and Asker C), density, abrasion resistance, compression set, shrinkage, rebound and biobased carbon content, and the results are shown in Table 6.

TABLE 6

| Properties of expanded polymer compositions | | | | | |
|---|---|---|---|---|---|
| Properties | Unit | C3 | C4 | C5 | C6 |
| Expansion Rate | % | 40 | 60 | 80 | 45 |
| Hardness Asker C | Asker C | 54 | 42 | 26 | 59 |
| Hardness Shore A | Shore A | 35 | 26 | 16 | 43 |
| Density | g/cm$^3$ | 0.281 | 0.2 | 0.123 | 0.268 |
| Abrasion | mm$^3$ | 87 | 134 | 215 | 85 |
| Compression Set | % | 54 | 60 | 67 | 52 |
| Shrinkage | % | 0.5 | 1 | 1 | 1 |
| Rebound | % | 42 | 45 | 49 | 41 |
| Biobased carbon content | % | 46 | 46 | 46 | 66 |

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A process for producing a polymer composition, comprising:
   fermenting a renewable source of carbon to produce ethanol;
   dehydrating the ethanol to produce bio-based ethylene;
   polymerizing ethylene at least partially comprising the bio-based ethylene with vinyl acetate to produce an ethylene vinyl acetate copolymer; and
   mixing the ethylene-vinyl acetate copolymer with an elastomeric polyolefin to produce an elastomeric ethylene-vinyl acetate,
   wherein a number average molecular weight (Mn) of the ethylene vinyl acetate copolymer is in a range of from 5 kilodaltons to 50 kilodaltons.

2. The process of claim 1, wherein the elastomeric polyolefin comprises an ethylene alpha-olefin copolymer and rubber.

3. The process of claim 1, wherein the mixing comprises mixing:
   the EVA copolymer at a percent by weight in the range of 20 wt % to 90 wt %;
   an ethylene alpha-olefin copolymer at a percent by weight in the range of 5% to 60%;
   a polyorganosiloxane at a percent by weight in the range of 0.1 wt % to 10 wt %;
   a plasticizer at a percent by weight in the range of 0.5 wt % to 20 wt %; and
   a rubber at a percent by weight in the range of 0.5 wt % to 40 wt %.

4. The process of claim 1, wherein the polymer composition exhibits a biobased carbon content as determined by ASTM D6866-18 Method B of at least 5%.

5. The process of claim 1, wherein the vinyl acetate is at least partially obtained from a renewable source of carbon.

6. The process of claim 1, wherein the fermenting produces the ethanol and a mixture of byproducts comprising higher alcohols, and the dehydration produces ethylene and higher alkene impurities, wherein the process further comprises: purifying the ethylene and higher alkene impurities in order to obtain the ethylene.

7. The process of claim 1, wherein the fermenting produces the ethanol and byproducts comprising higher alcohols, wherein the process further comprises: purifying the ethanol and byproducts in order to obtain the ethanol.

8. The process of claim 1, wherein the renewable source of carbon is at least one plant material selected from the group consisting of sugar cane and sugar beet, maple, date palm, sugar palm, sorghum, American agave, corn, wheat, barley, sorghum, rice, potato, cassava, sweet potato, algae, fruit, materials comprising cellulose, wine, materials comprising hemicelluloses, materials comprising lignin, wood, straw, sugarcane bagasse, sugarcane leaves, corn stover, wood residues, paper, and combinations thereof.

9. The process of claim 1, wherein the process further comprises: curing the polymer composition in the presence of a peroxide agent.

10. The process of claim 1, wherein the process further comprises: curing and expanding the polymer composition in the presence of at least a blowing agent and a peroxide agent.

11. The process of claim 10, wherein the curing of the polymer composition occurs in a full or partial presence of oxygen.

12. The process of claim 1, wherein the polymerizing is at a temperature of from 80° ° C. to 300° ° C.

13. The process of claim 1, wherein the polymerizing is at a pressure of from 500 bar to 3000 bar.

14. The process of claim 1, wherein the polymerizing comprises a radical polymerization or a solution polymerization.

15. The process of claim 1, wherein the polymerizing is in the presence of one or more free-radical producing agent.

16. The process of claim 1, wherein the process further comprises: curing the polymer composition in the presence of a crosslinking co-agent.

17. The process of claim 1, wherein the polymer composition produces a reduced concentration of carbon dioxide having a fossil origin compared to a polymer composition exhibiting a biobased carbon content of 0%.

18. The process of claim 1, wherein the vinyl acetate is present in the ethylene vinyl acetate copolymer in an amount ranging from 5 to 40 wt % and the ethylene is present in the ethylene vinyl acetate copolymer in an amount ranging from 60 to 95 wt %.

19. The process of claim 2, wherein the ethylene alpha-olefin copolymer is prepared from a $C_3$ to $C_{20}$ alpha-olefin monomer.

* * * * *